(12) United States Patent
Finke

(10) Patent No.: US 9,125,992 B2
(45) Date of Patent: Sep. 8, 2015

(54) FLUID DELIVERY DEVICE WITH FILTRATION

(76) Inventor: Melvin A. Finke, DeLand, FL (US)

( * ) Notice: Subject to any disclaimer, the term of this patent is extended or adjusted under 35 U.S.C. 154(b) by 834 days.

(21) Appl. No.: 13/234,225

(22) Filed: Sep. 16, 2011

(65) Prior Publication Data

US 2013/0072880 A1 Mar. 21, 2013

(51) Int. Cl.
| | |
|---|---|
| A61M 5/178 | (2006.01) |
| B23K 26/384 | (2014.01) |
| A61M 5/31 | (2006.01) |
| B23K 26/40 | (2014.01) |
| B23K 26/38 | (2014.01) |
| A61M 5/32 | (2006.01) |
| A61M 39/22 | (2006.01) |

(52) U.S. Cl.
CPC ............... *A61M 5/3145* (2013.01); *A61M 5/32* (2013.01); *B23K 26/383* (2013.01); *B23K 26/4065* (2013.01); *A61M 5/3293* (2013.01); *A61M 39/223* (2013.01); *B29C 2791/009* (2013.01); *B29C 2793/0018* (2013.01)

(58) Field of Classification Search
CPC .................... A61M 5/3145; A61M 2005/1652
See application file for complete search history.

(56) References Cited

U.S. PATENT DOCUMENTS

| | | |
|---|---|---|
| 2,512,568 A | 6/1950 | Saffir |
| 2,541,272 A | 2/1951 | Murphy |
| 2,590,895 A | 4/1952 | Scarpellino |
| 2,746,455 A | 5/1956 | Abel |
| 2,752,919 A | 7/1956 | Gabriel |
| 2,778,360 A * | 1/1957 | Miskel ............................. 604/87 |
| 2,954,768 A | 10/1960 | Hamilton |
| 3,076,457 A | 2/1963 | Copen |
| 3,119,391 A | 1/1964 | Harrison |
| 3,524,046 A * | 8/1970 | Brouwer ........................ 219/384 |
| 3,662,754 A | 5/1972 | Halloran |
| 3,776,239 A | 12/1973 | Cooley |
| 3,817,389 A | 6/1974 | Weichselbaum |
| 3,831,814 A | 8/1974 | Butler |
| 4,058,121 A | 11/1977 | Choksi et al. |
| 4,287,065 A | 9/1981 | Raines |
| 4,316,462 A | 2/1982 | Baker |
| 4,387,879 A | 6/1983 | Tauschinski |
| 4,505,709 A | 3/1985 | Froning et al. |
| 4,610,683 A | 9/1986 | Vaillancourt |
| 4,619,651 A | 10/1986 | Kopfer et al. |
| 4,675,017 A | 6/1987 | Sato |
| 4,675,020 A | 6/1987 | McPhee |
| 4,682,980 A | 7/1987 | Suzuki |

(Continued)

FOREIGN PATENT DOCUMENTS

FR 2845276 A1 4/2004

OTHER PUBLICATIONS

European Search Report No. EP06251039 2 pages; dated Jun. 9, 2006.

(Continued)

*Primary Examiner* — Christina Johnson
*Assistant Examiner* — David Schmerfeld
(74) *Attorney, Agent, or Firm* — Lisa E. Winsor, Esq.

(57) ABSTRACT

This disclosure relates to fluid delivery devices which include a body defining a fluid channel with filtration. In one embodiment, the body is molded to include a barrier which extends across the fluid channel and a series of apertures or openings are formed through the barrier. A laser device may be used to form the apertures through the barrier.

6 Claims, 6 Drawing Sheets

(56) References Cited

U.S. PATENT DOCUMENTS

| | | |
|---|---|---|
| 4,710,180 A | 12/1987 | Johnson |
| 4,723,955 A | 2/1988 | Vaillancourt |
| 4,743,243 A | 5/1988 | Vaillancourt |
| 4,756,780 A | 7/1988 | Sato |
| 4,820,276 A | 4/1989 | Moreno |
| 4,834,149 A | 5/1989 | Fournier et al. |
| 4,834,152 A | 5/1989 | Howson et al. |
| 4,838,877 A | 6/1989 | Massau |
| 4,842,591 A | 6/1989 | Luther |
| 4,990,140 A | 2/1991 | Black |
| 5,024,657 A | 6/1991 | Needham et al. |
| 5,059,172 A | 10/1991 | Sutherland et al. |
| 5,071,413 A | 12/1991 | Utterberg |
| 5,167,642 A | 12/1992 | Fowles |
| 5,188,620 A | 2/1993 | Jepson et al. |
| 5,203,775 A | 4/1993 | Frank et al. |
| 5,211,638 A | 5/1993 | Dudar et al. |
| 5,215,529 A | 6/1993 | Fields et al. |
| 5,242,411 A | 9/1993 | Yamamoto et al. |
| 5,364,387 A | 11/1994 | Sweeney |
| 5,470,327 A | 11/1995 | Helgren et al. |
| 5,584,819 A | 12/1996 | Kopfer |
| 5,746,733 A | 5/1998 | Capaccio et al. |
| 5,755,696 A | 5/1998 | Caizza |
| RE35,841 E | 7/1998 | Frank et al. |
| 5,820,621 A | 10/1998 | Yale et al. |
| 5,832,971 A | 11/1998 | Yale et al. |
| 5,833,674 A | 11/1998 | Turnbull et al. |
| 5,887,633 A | 3/1999 | Yale et al. |
| 5,919,182 A | 7/1999 | Avallone |
| 5,928,162 A | 7/1999 | Giurtino et al. |
| 5,928,215 A | 7/1999 | Caizza et al. |
| 5,976,115 A | 11/1999 | Parris et al. |
| 6,008,468 A * | 12/1999 | Tanaka et al. ............ 219/121.71 |
| 6,139,534 A | 10/2000 | Niedospial, Jr. et al. |
| 6,206,858 B1 | 3/2001 | Kempen et al. |
| 6,358,236 B1 | 3/2002 | DeFoggi et al. |
| 6,394,979 B1 | 5/2002 | Sharp et al. |
| 6,447,498 B1 | 9/2002 | Jepson et al. |
| 6,503,240 B1 | 1/2003 | Niedospial, Jr. et al. |
| 6,544,246 B1 | 4/2003 | Niedospial, Jr. |
| 6,565,591 B2 * | 5/2003 | Brady et al. .................. 606/200 |
| 6,585,697 B2 | 7/2003 | Kempen et al. |
| 6,610,041 B2 | 8/2003 | Daubert et al. |
| 6,616,632 B2 | 9/2003 | Sharp et al. |
| 6,635,043 B2 | 10/2003 | Daubert et al. |
| 6,637,470 B2 | 10/2003 | Reihl et al. |
| 6,715,520 B2 | 4/2004 | Andréasson et al. |
| 6,832,994 B2 | 12/2004 | Niedospial, Jr. et al. |
| 6,875,205 B2 | 4/2005 | Leinsing |
| 6,921,395 B2 | 7/2005 | Carano et al. |
| 6,976,604 B2 * | 12/2005 | Connors et al. ................ 220/713 |
| 7,077,835 B2 | 7/2006 | Robinson et al. |
| 7,540,388 B2 * | 6/2009 | Silver ............................ 215/11.1 |
| 2002/0019622 A1 | 2/2002 | Daubert et al. |
| 2004/0024354 A1 | 2/2004 | Reynolds |
| 2004/0039365 A1 | 2/2004 | Aramata et al. |
| 2007/0078428 A1 | 4/2007 | Reynolds et al. |

OTHER PUBLICATIONS

Sherwood Medical Industries, Inc., Monoject Product Data Filter Aspiration Needle, Aug. 1973, 1 page.

Sherwood Medical Industries, Monoject Filter Aspiration Needle, An Efficient Stainless Steel Filter in a Needle Hub, 1 page.

* cited by examiner

FLUID DELIVERY DEVICE WITH FILTRATION

BACKGROUND

1. Technical Field

The present disclosure relates to fluid delivery devices for medical use. More particularly, the present disclosure relates to fluid delivery devices, such as needle assemblies or syringes, which include integral structure for providing fluid filtration.

2. Background of Related Art

Fluid delivery devices for communicating or directing a fluid to a desired location are well known in a variety of different technological areas. In the medical arts, fluid delivery devices include syringes, luer hubs, stopcocks, intravenous ("I.V.") line connectors, feeding set connectors and the like. Such devices are typically used to supply a parenteral solution from a source, such as a syringe, to a patient. As used herein, parenteral solutions is intended to refer to any solution intravenously or intramuscularly fed to a patient, such as via a syringe or intravenous infusion set.

Liquid formulations of drugs are seldom stable over prolonged periods of time. Thus, it is common for a drug to be provided in solid form, e.g., lyophilized (freeze dried), dehydrated or crystalline form. Such drugs require reconstitution, i.e. mixing the drug with a diluent, e.g., a dextrose solution, a saline solution or water, before the drug can be delivered to a patient. This can be accomplished by injecting the diluent into a vial containing the drug in solid form and thereafter shaking the vial or allowing the vial to sit for a predetermined period of time to ensure dissolution of the drug and the diluent. After the drug has been reconstituted, the drug can be withdrawn from the vial using, for example, a syringe, and delivered intravenously to a patient.

One problem associated with the above-described process is the presence of particulate contamination in the parenteral solution infused or injected into patients and the possible harm it may cause to a patient. Particulate contamination may also result from damaged syringes or the like unrelated to reconstitution of drugs. In order to minimize the risk associated with particulate contamination, it is known to press-fit a stainless steel mesh having, for example, 100 count mesh into an aluminum needle hub. Although such needle hubs provide filtration, the provision of a secondary filter in the needle hub, or like fluid devices, is costly.

Accordingly, a continuing need exists for a less costly fluid delivery device for delivering parenteral solutions which provides filtration.

SUMMARY

A fluid delivery device is disclosed which includes a body defining a fluid channel, a barrier formed integrally with the body extending across the fluid channel and a plurality of apertures formed through the barrier to define a filtered opening. The filtered opening facilitates fluid flow through the fluid channel. In one embodiment, the filtered opening has a count mesh of between and including about 50 and 200 mesh, wherein the count mesh number defines the number of apertures in a filter of one inch diameter. The body and the barrier may be integrally molded and the plurality of apertures may be formed in the barrier using a directed energy device.

In one embodiment, the body defines a needle hub and includes a proximal end including a luer type connector and a distal end supporting a needle cannula. The proximal end of the needle hub may define an inwardly tapered bore for receiving the end of a fluid delivery device, e.g., a syringe, and the distal end may define a bore dimensioned to receive the proximal end of the needle cannula.

In another embodiment, the body is configured as a vial access device and includes a proximal portion which defines a luer type connector and a distal end defining a cannula. The cannula may define a blunt distal edge and may include at least one side opening which communicates with the fluid channel.

In yet another embodiment, the body may define a cylindrical valve member, and the fluid delivery device may further include a housing defining a cylindrical receptacle for rotatably receiving the cylindrical valve member. In such an embodiment, the housing may include a fluid inlet and a fluid outlet such that the cylindrical valve member is being movable from a first position in which the fluid channel of the body is aligned with the fluid inlet and the fluid outlet to a second position in which the fluid channel is misaligned with the fluid inlet and the fluid outlet.

In another embodiment, the fluid channel of the cylindrical valve member may include a Y-shaped bore having a first inlet opening, a second inlet opening and an elongated outlet opening, wherein the filtered opening extends across the second inlet opening.

The cylindrical valve member may include an actuator arm to facilitate rotation of the cylindrical valve member. In addition, the fluid outlet may define a vial access cannula.

In one embodiment, the body is molded from a polyolefin such as polypropylene or polyethylene.

A method of forming a fluid delivery device is also disclosed which includes the steps of molding a body defining a fluid channel and having a barrier extending across the fluid channel and forming a plurality of apertures through the barrier to define a filtered opening to facilitate fluid flow through the fluid channel.

BRIEF DESCRIPTION OF THE DRAWINGS

Various embodiments of the presently disclosed fluid delivery device with filtration are described herein with reference to the drawings wherein.

DETAILED DESCRIPTION

Embodiments of the presently disclosed fluid delivery device with filtration are described in detail herein with reference to the drawings wherein like reference numerals identify similar or identical elements in each of the several views. A fluid delivery device may be any device suitable for delivering or transferring a liquid into or out of a liquid reservoir, such as diluents used to reconstitute a drug, or a reconstituted drug. Examples of fluid transfer devices include syringes, luer hubs, stopcocks, intravenous line adaptors, feeding set adaptors, and vial access adaptors. As used herein, the term "distal" refers to that portion of the device which is further from a user while the term "proximal" refers to that portion of the device which is closer to a user.

Figure 1:
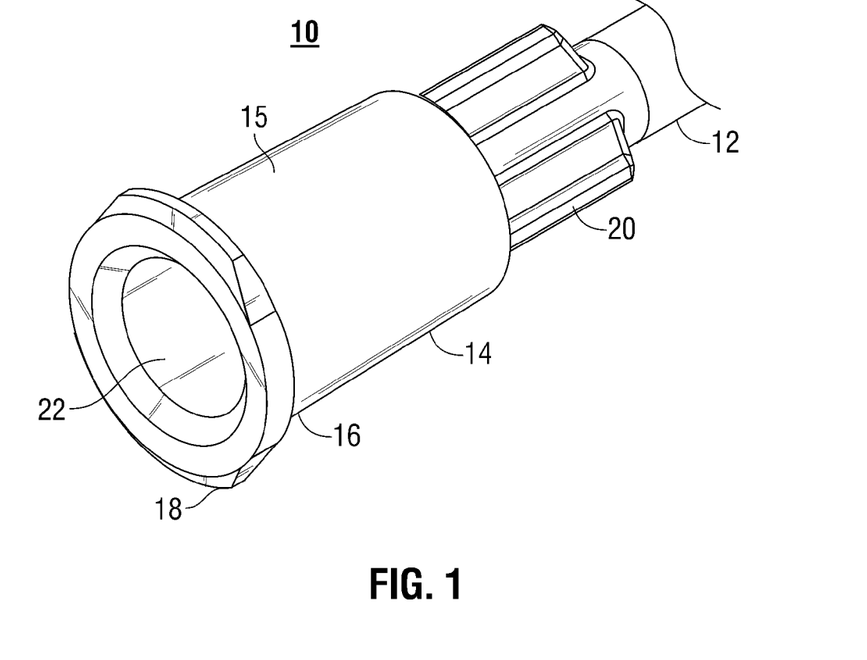
FIG. 1 is a perspective view of one embodiment of the presently disclosed fluid delivery device with filtration including a needle assembly having a needle hub and a needle cannula.
Figure 2:
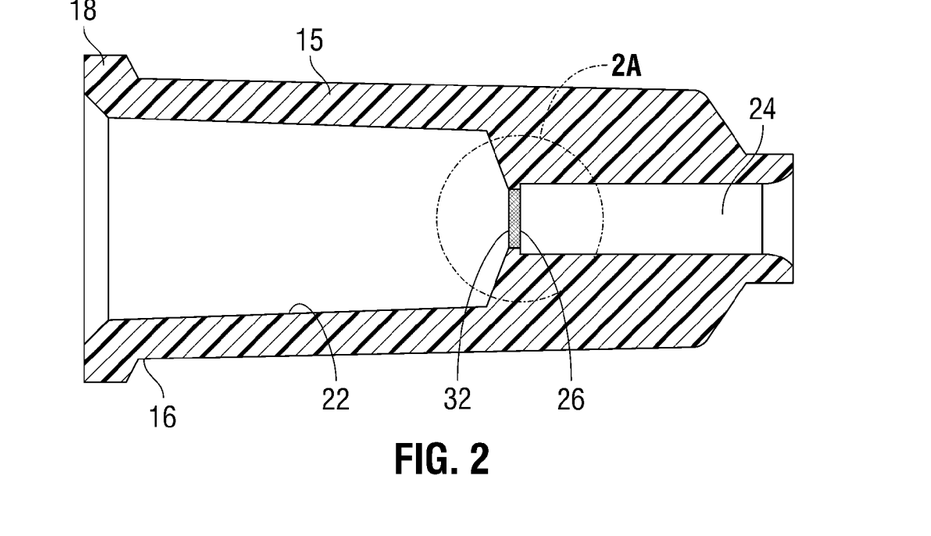
FIG. 2 is a side cross-sectional view of the needle hub of the needle assembly shown in FIG. 1.
Figure 2A:
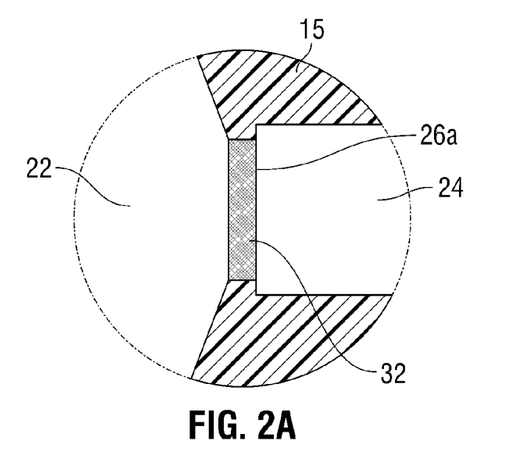
FIG. 2A is an enlarged view of the indicated area of detail shown in FIG. 2 illustrating the filtered opening.

Referring to FIGS. 1-2A, in one embodiment, the presently disclosed fluid delivery device, shown generally as 10, includes a needle cannula 12 and a needle hub 14. Needle cannula 12 defines a fluid channel (not shown). The needle hub 14 includes a body 15 which may be molded from a polyolefin such as polypropylene or polyethylene. Alternately, it is envisioned that other materials of construction may be used to construct body 15, e.g., polycarbonates. The needle hub 14 includes a proximal end 16 defining a connector 18 and a distal end 20. Connector 18 may be any conventional connector such as male or female luer connector, snap or friction fit. In one embodiment shown in FIGS. 1-2A, connector 18 is a male luer type connector. Proximal end 16 defines a bore 22 configured to receive the fluid outlet of a fluid transfer apparatus, such as, a syringe barrel, and an I.V. line connector. Distal end 20 defines a smaller diameter bore 24 (FIG. 2) which may be dimensioned to receive a proximal end of needle cannula 12. In one embodiment shown in FIGS. 1-2A, the sidewall of bore 22 may provide an inwardly tapered bore, having an inner diameter adjacent the proximal end larger than an inner diameter adjacent the distal end. Bores 22 and 24 define a fluid channel which extends through the body 15. In one embodiment, the proximal end of the needle cannula 12 may be securely fixed within bore 24 using adhesives, crimping or the like.

In one embodiment, body 15 is initially molded to include a barrier 26 (FIG. 2B) which encloses the proximal end of bore 24 and the distal end of bore 22 forming a fluid tight seal between bore 24 and bore 22. Barrier 26 may have any thickness suitable for a desired purpose. Barrier 26 may comprise a first surface 40 opposite bore 22 and a second surface 42 opposite bore 24. First and second surfaces 40, 42 may be substantially planar positioned perpendicularly to bores 22 and 24, respectively. Alternatively, at least one of the first surface 40 and the second surface 42 may be convex or concave. The first surface 40 and the second surface 42 may, but need not, be similarly shaped. That is the first and second surfaces may, but need not, both be either planar, convex, or concave. A barrier having a convex surface facing a fluid to be filtered provides a larger surface area to provide filtration orifices and may reduce or eliminate the possibility of one or more orifices clogging during filtration. The degree of concavity of the surface and the number and size of the orifices may be such that the filter may not substantially restrict the flow of fluid between bore 22 and bore 24.

Figure 2B:
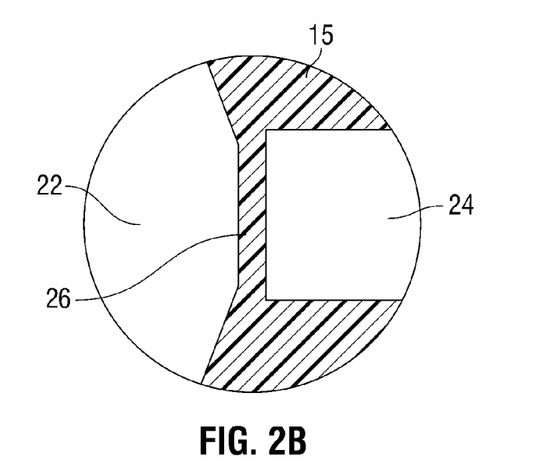
FIG. 2B is an enlarged view of the indicated area of detail shown in FIG. 2A prior to formation of apertures in the filtered opening.

Thereafter, a directed energy source, such as a krypton arc or xenon arc laser (not shown) which may be positioned adjacent one of the proximal end and distal end of body 15 during and/or after the formation process, is operated or actuated to form or drill a plurality of holes or apertures 26a through barrier 26 to define a filtered opening 32. In one embodiment, the laser may be fixed to the proximal end of body 15 during the formation process. The filtered opening 32 is integrally formed with the body 15 of the needle hub 14.

The filtered opening 32 may comprise a plurality of apertures extending between first surface 40 and second surface 42 of barrier 26. In one embodiment, filtered opening 32 is constructed and arranged so that it does not substantially impede the flow of fluid between the first bore 22 and the second bore 24. The plurality of apertures may be positioned throughout the barrier in any desired pattern suitable for a particular purpose. The plurality of apertures may be positioned in a random pattern or in a regular repetitive pattern. The density of the orifices may be uniform or may vary throughout the barrier. For example, barrier 26 may have a larger number of apertures at or adjacent a central region of the barrier than the number of orifices at or adjacent a perimeter of the barrier. The plurality of apertures may have any size and shape suitable for a particular purpose, such as circles, ovals, squares, triangles, rectangles, crosses. Each of the plurality of apertures may, but need not, be similarly sized and shaped.

Figure 2C:
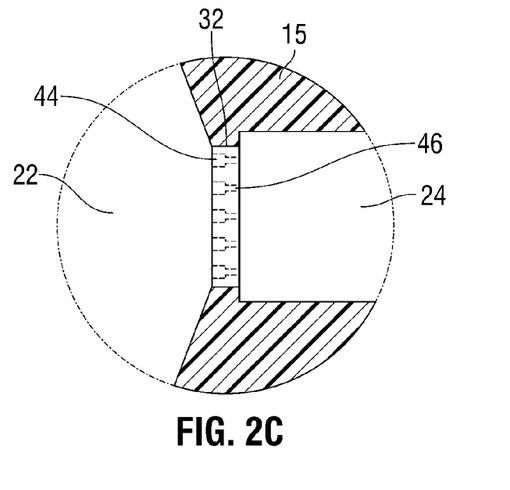
FIG. 2C is a cross sectional view of one embodiment of a filter opening of the present invention.

In another embodiment shown in FIG. 2C, filtered opening 32 may comprise one or more sections comprising apertures having different cross sectional areas along its axis, thereby providing a depth filter. In FIG. 2C, a first portion of filtered opening 32 may comprise first cavities 44 on first surface 40 which may have a cross sectional area greater than the cross sectional area of second cavities 46 on second surface 46 of a second portion of filtered opening 32. First cavities 44 may have a first depth less than the total thickness of barrier 26 extending between the first surface and the second surface. Second cavities 46 may have a second depth less than the total thickness of barrier 26 extending between the first surface and the second surface. The sum of the first depth and the second depth will equal the total thickness of barrier 26. The first depth and the second depth may, but need not, be substantially the same. In one embodiment, the first depth may be greater than the second depth. In another embodiment, the second depth may be greater than the first depth. It is understood that a first cavity may have one or more second cavities extending therefrom. In one embodiment, the second cavities may have a diameter of five (5) microns. In one embodiment, not shown, two second cavities are formed at a base of one first cavity.

In another embodiment, the filtered opening may comprise three or more sections, each section comprising apertures having cross sectional areas different from the cross sectional areas in another cross sectional area. The configuration of each of each section may provide desired filtering properties. The configuration of each section may assist in the orientation of chemical or medicinal strands present in the medicament to be delivered. Orientation of strand may allow the delivery of complex medicaments comprising long strands of an active ingredient through different gauge needles. For example, the use of a filtered opening 32 which comprises one or more sections, each section having apertures having a particular cross sectional area, may result in orientation of long strand medicaments which may be delivered through a higher gauge needle, thereby reducing overall needle diameters and potentially the pain associated with the use of larger diameter needles.

Filtered opening 32 having different cross sectional areas along its axis may be formed with a directed energy source, such as a krypton arc or xenon arc laser (not shown) which may be positioned adjacent one of the proximal end and distal end of body 15 during and/or after the formation process, is configured and operated or actuated to form or drill a first cavity 44 to a desired depth in barrier 26. Subsequently, the directed energy source may be configured and operated or actuated to form or drill a second cavity 46 from the base of the first cavity 44 through the barrier 26. Alternatively, a first directed energy source may be actuated toward a first surface 40 of barrier 36 and a second directed energy source may be actuated toward a second surface 46 of barrier 26 to simultaneously or subsequently form a cavity of a desired depth on each surface.

The filtered opening 32 may be formed to have a "count mesh" number of between about 50 and 200 and may be about 100, wherein the "count mesh" number defines the number of apertures or openings which would be formed in a filter of one inch diameter. Alternately, other precise drilling techniques may be used to form the openings 26a. Other "count mesh" numbers may be selected depending on the intended use of the fluid delivery device. In one embodiment, the openings 26a and/or first or second cavities 44, 46 may be as small as 5 microns.

Each of the apertures may, but need not, be aligned perpendicularly to at least one of the first surface 40 and the second surface 42 of barrier 26. In one embodiment, barrier 26 comprises a plurality of apertures extending perpendicularly between first planar surface 40 and a second planar 42 of barrier 26. Apertures may have a regular or irregular cross sectional shape suitable for a desired purpose, such as circle, square, triangle, trapezoid or star. Moreover, each aperture may, but need not, have the same cross sectional shape. In one embodiment, each aperture is circular. In another embodiment, shown in FIG. 2B barrier 26 may comprise a plurality of apertures extending between a first planar surface 44 and a second convex surface 46 constructed an arranged such that a passageway 48 or each orifice is substantially perpendicular to a tangent of the convex surface. Although the plurality of passageways 48 are shown to converge into one opening in the first surface 40, in other embodiments, at least one or all of the passageways may comprise individual apertures at the first surface 40. In use, a connector, such as a female luer connector, of a syringe barrel or other fluid transfer apparatus including a diluent (not shown) may be secured to the male luer connector 18 of body 15 of needle hub 14. The needle cannula 12 can be inserted through the stopper or septum of a medical vial (not shown) to inject the diluent into the medical vial. As the diluent is injected from the syringe through the needle hub 14 and needle cannula 12 and into the vial, the diluent will pass through the filtered opening 32. Likewise, when the reconstituted medical fluid is withdrawn from the vial into the syringe through needle hub 14 and needle cannula 12, the reconstituted fluid will pass through the filtered opening 32, but may prevent passage of at least a portion of particulate contamination which may be present in the reconstituted medical fluid, present in a reconstitution vial and/or in a fluid transfer apparatus such as a syringe barrel and an I.V. line adaptor. As used herein, "particulate contamination" is defined as the presence of a drug in solid form may not be completely dissolved by the diluent, and/or the presence of solids coming from one or more of a needle cannula, syringe barrel, plunger, and a stopper of a medical vial.

Although the needle cannula 12 and needle hub 14 are described above in a reference to a process for reconstituting a drug, the needle cannula 12 and needle hub 14 may be used to deliver a wide variety of parenteral solutions. In addition to preventing of at least a portion of particulate contamination from being withdrawn from a medical vial, the needle cannula 12 and needle hub 14 including filtered opening 32 will also prevent delivery to a subject of at least a portion of particulate contamination that results from a variety of different defects such as, for example, defective syringes barrels, plungers, or the like, which may contact the reconstituted fluid upon being drawn into a syringe barrel.

Figure 3:
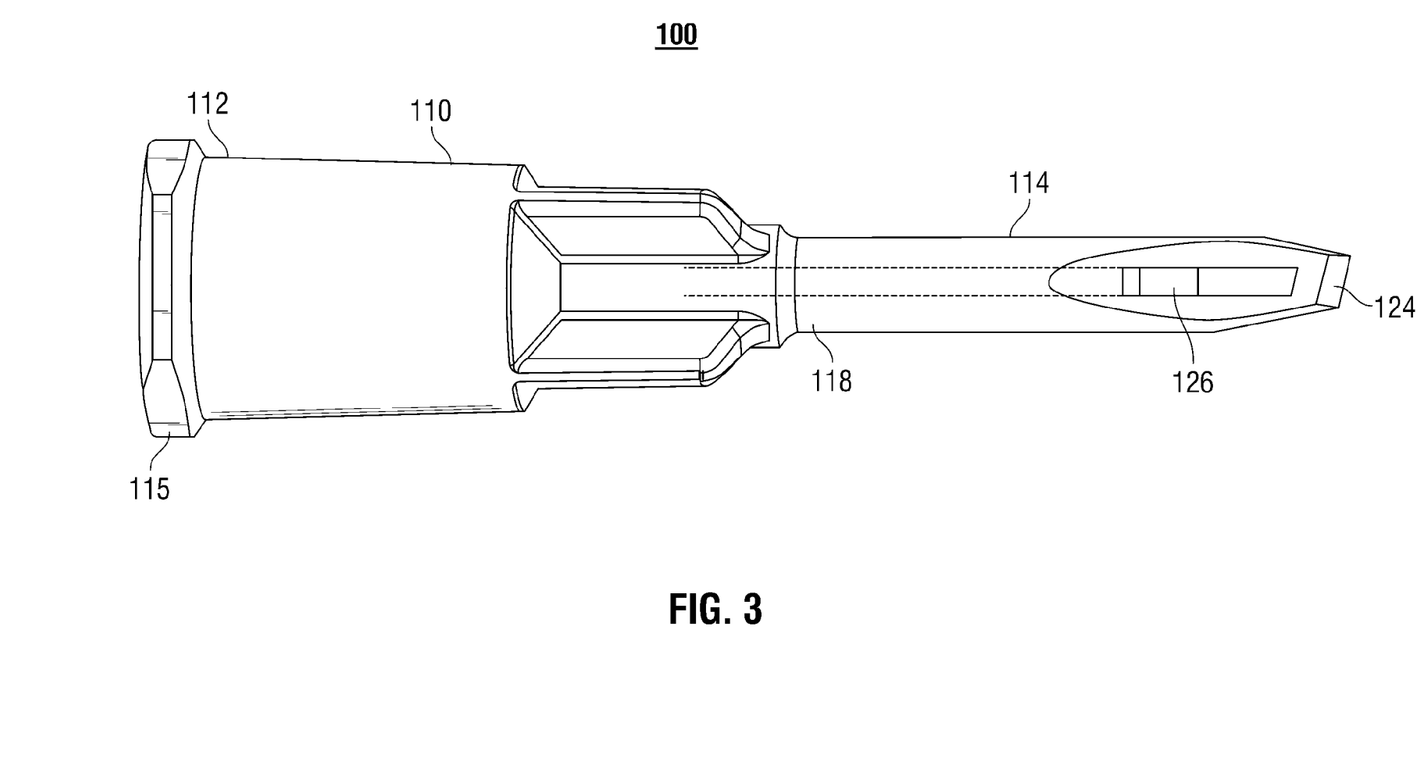
FIG. 3 is a side view of another embodiment of the presently disclosed fluid delivery device with filtration including a vial access cannula.
Figure 4:
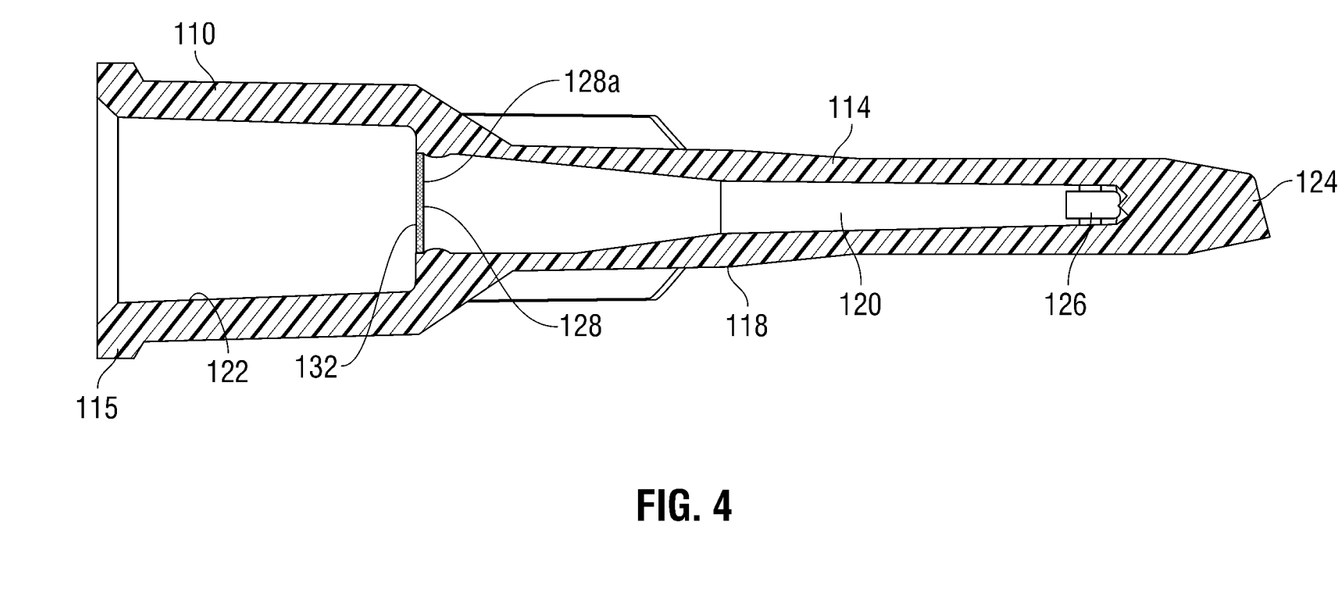
FIG. 4 is a side cross-sectional view of the vial access cannula shown in FIG. 3.

FIGS. 3 and 4 illustrate an alternative embodiment of a fluid delivery device with filtration, shown generally as 100. Fluid delivery device 100 is configured as a vial access cannula and includes a body 110 which may be molded from a polyolefin, or other material, as discussed above with respect to body 15 of needle hub 14. Body 110 includes a proximal portion 112 and a distal portion 114. Proximal portion 112 defines a connector 115 and a bore 122. Connector 115 may be any suitable connector such as a male luer connector, female luer connector, snap connector, and a friction connector, configured to mate with a fluid outlet of a fluid transfer apparatus, such as a syringe barrel and an I.V. line connector. In one embodiment shown in FIG. 3, connector 115 is a male luer connector and the sidewall of bore 122 may provide an inwardly tapered bore, having an inner diameter adjacent the proximal end larger than an inner diameter adjacent the distal end.

Distal portion 114 may include a blunt cannula 118 which may define a smaller diameter bore 120. Bores 120 and 122 define a fluid channel through body 110. The distal end of distal portion 114 defines an edge 124 configured to pierce a stopper of a vial. At least one side opening 126 extends through an outer wall of distal portion 114 and communicates with fluid channel 120.

As shown in FIG. 4, a barrier 128 is formed between the proximal end of bore 120 and the distal end of bore 122. Barrier 128 is identical in configuration and methods of manufacture to the configuration and methods of manufacture of barrier 26 of needle hub 14 described above. Specifically, barrier 128 can be molded integrally with device 100. Thereafter, a plurality of orifices 128a can be formed in the barrier 128 to define a filtered opening 132. In one embodiment, the openings or apertures 128 are formed or drilled in barrier 128 using a laser to have a preselected "count mesh" number or other desired configuration similar to configuration of barrier 26 described above.

In addition to, or as a replacement for, filtered opening 132, one or more side openings 126 may also be formed as a filter.

Although vial access cannula or device 100 is described to have a specific configuration, it is envisioned that the device may assume a variety of configurations and is not limited to the specific configuration described and illustrated herein. For example, distal portion 114 may include a sharper configuration or have distally located openings. In use, the connector 115 of vial access cannula or device 100 is secured to a fluid transfer apparatus such as a syringe barrel (not shown) and operated in a manner substantially similar to that discussed above with respect to device 10.

Although fluid transfer devices 10 and 100 are shown with connectors to mate with a syringe barrel, in other embodiments, needle hub may be directly fixed to a syringe barrel.

Figure 5:
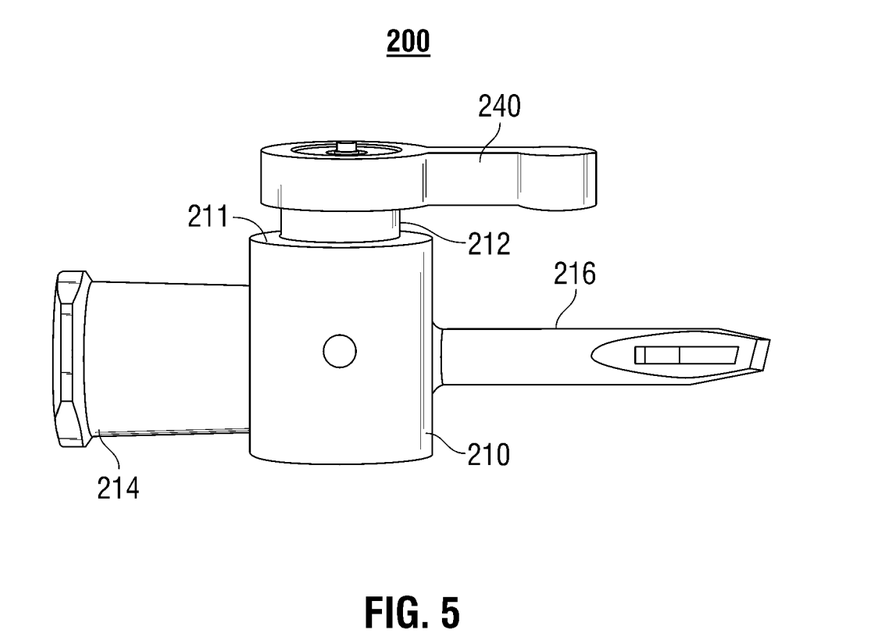
FIG. 5 is a side view of yet another embodiment of the presently disclosed fluid delivery device including a stopcock valve.
Figure 5A:
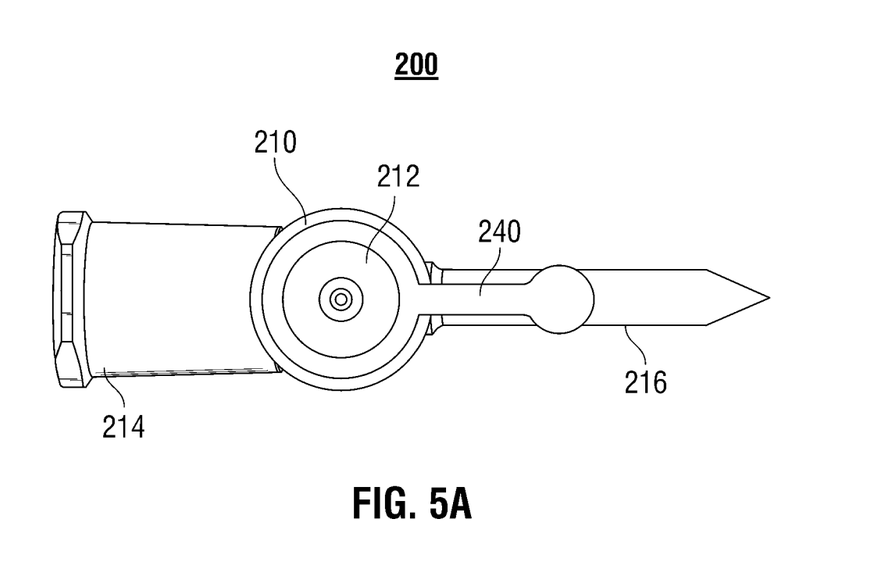
Figure 6:
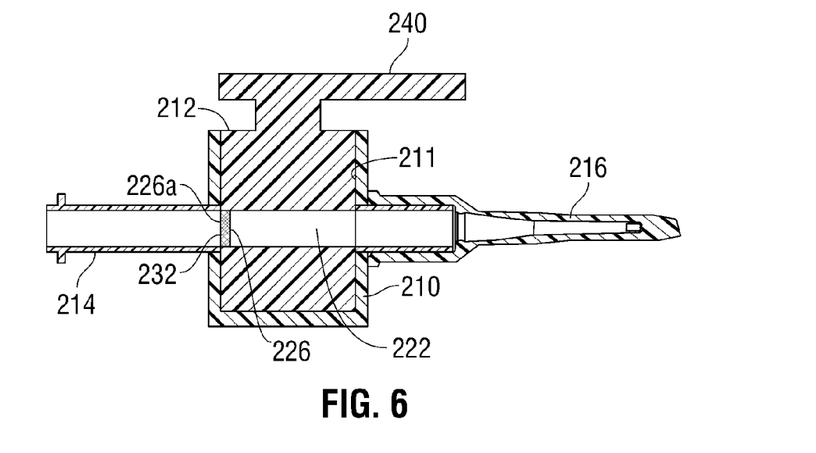
FIG. 6 is a side cross-sectional view of the stop-cock valve with the valve member separated from the valve housing.

FIGS. 5 and 6 illustrate an alternative embodiment of the presently disclosed fluid delivery device with filtration configured as a stop-cock valve shown generally as 200. As shown, stop-cock valve 200 includes a housing 210 and a rotatable valve member 212. Housing 210 defines a cylindrical receptacle 211 and includes a fluid inlet member 214 and a fluid outlet member 216. Fluid inlet member 214 includes a male luer type connector 218. Fluid inlet member 214 and fluid outlet member 216 communicate with cylindrical receptacle 211. Rotatable valve member 212 includes a cylindrical valve body 220 which is rotatably received within the receptacle 211. Valve member 212 defines a single bore 222 including a barrier 226 integrally formed with valve member 212. Barrier 226 includes a plurality of openings or apertures 226a to define a filtered opening 232.

In use, the rotatable valve member 212 is rotatably positioned within the receptacle 211 and is rotatable from a first position in which bore 222 is aligned with fluid inlet member 214 and fluid outlet member 216 to permit fluid to flow from the fluid inlet member 214 to the fluid outlet member 216, to a second position in which the bore 222 is misaligned with the fluid inlet member 214 and the fluid outlet member 216 to prevent fluid from flowing between the fluid inlet member 214 and the fluid outlet member 216. As is evident, when the valve member 212 is in its first position, fluid flowing from the fluid inlet 214 to the fluid outlet must flow through filtered opening 232.

In one embodiment, the stop-cock valve 200 is molded from a polyolefin such as polypropylene or polyethylene, although other materials of construction are envisioned. The rotatable valve member 212 may be molded to include bore 222 and barrier 226. Thereafter, openings or apertures 226a may be formed through barrier 226 to define a desired "count mesh" number, e.g., 100, using, as discussed above, a laser drilling process. Alternately, other precise drilling techniques may be used to form the openings 226a.

In one embodiment, the rotatable valve member 212 includes an actuator arm 240. Actuator arm 240 may be integrally formed with the valve member 212 and can be gripped by an operator to move the rotatable valve member 212 between its first and second positions. Alternately, actuator arm 240 can be formed separately from valve member 212 and can be secured to the valve member 212 using other known securement techniques, e.g., screws, pins, etc.

Figure 7:
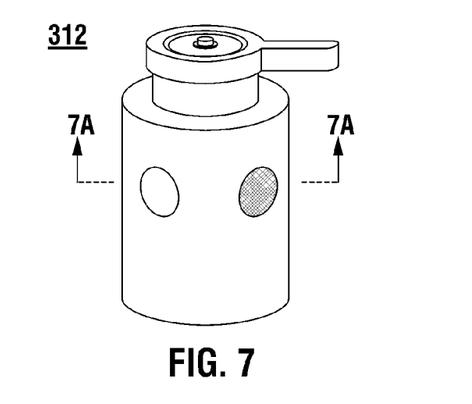
FIG. 7 is a side perspective view of an alternative embodiment of the valve member shown in FIG. 6.
Figure 7A:
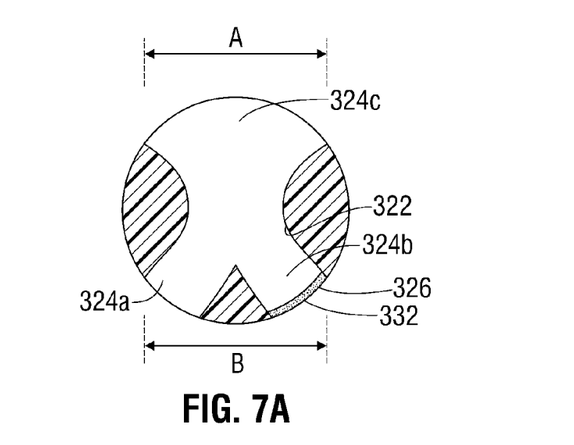
FIG. 7A is a cross-sectional view taken along section lines 7A-7A of FIG. 7.

FIG. 7 illustrates an alternative embodiment of the rotatable valve member shown generally as 312. Valve member 312 is similar to valve member 212 but includes a Y-shaped bore 322 rather then a linear bore 222. Y-shaped bore 322 includes a first inlet opening 324a, a second inlet opening 324b and an elongated outlet opening 324c. Outlet opening 324c fluidly communicates with each inlet opening 324a and 324b. A barrier 326 defining a filtered opening 332 is positioned in the inlet end of opening 324b. In use, valve member 312 is rotatable from a first position to align first inlet opening 324a with fluid inlet member 214 and align elongated outlet opening 324c with fluid outlet member 216, to a second position in which second inlet opening 324b is aligned with fluid inlet member 214 and elongated outlet opening 324c is aligned with fluid outlet member 216, to a third position in which first and second inlet openings 324a and 324b are misaligned with the fluid inlet 214. See also FIG. 6. Thus, valve member 322 can provide non-filtered fluid flow, filtered fluid flow, and no flow.

Referring again to FIG. 6, fluid outlet member 216 may be configured as a vial access cannula such as shown in FIG. 4. Alternatively, fluid outlet member 216 may define a luer type connector, similar to fluid inlet member 214, to facilitate attachment to another medical device, such as, for example, an I.V. line connector.

It will be understood that various modifications may be made to the embodiments disclosed herein. For example, although illustrated and described with respect to three specific fluid delivery devices, the use of the presently disclosed integrally formed filtered opening may be incorporated into a variety of different types of fluid delivery devices. Therefore, the above description should not be construed as limiting, but merely as exemplifications of preferred embodiments. Those skilled in the art will envision other modifications within the scope and spirit of the claims appended hereto.

What is claimed is:

1. A method of forming a fluid delivery device comprising the following steps:
   molding a body defining a fluid channel and having a barrier extending across the fluid channel, wherein the body defines a needle hub and includes a proximal end including a luer type connector and a distal end configured to support a needle cannula and wherein the barrier is initially molded integrally with the body; and
   forming a plurality of apertures through the barrier to define a filtered opening to facilitate fluid flow through the fluid channel;
   wherein the step of forming a plurality of apertures includes:
   using a laser to form a series of apertures;
   forming a series of first cavities having a first cross-sectional area and a depth less than a thickness of the barrier; and
   forming at least one second cavity in each of the first cavities, wherein the at least one second cavity has a cross-sectional area less than the cross-sectional area of the first cavity.

2. The method according to claim 1, wherein a depth of the first cavity and a depth of the at least one second cavity formed in the first cavity equals the thickness of the barrier.

3. The method according to claim 1, wherein the first cavity and the at least one second cavity formed in the first cavity are formed simultaneously.

4. A method of forming a fluid delivery device comprising:
   molding a body defining a fluid channel therein and having a barrier extending across the fluid channel, wherein the body defines a needle hub and includes a proximal end including a luer type connector and a distal end supporting a needle cannula and wherein the barrier is initially molded integrally with the body; and
   forming a plurality of apertures through the barrier to define a filtered opening to facilitate fluid flow through the fluid channel, wherein the plurality of apertures has a count mesh size of from about 50 to about 200 mesh;
   wherein forming a plurality of apertures includes: using a laser to form the plurality of apertures through the barrier;
   forming a series of first cavities having a first cross-sectional area and a depth less than a thickness of the barrier; and
   forming at least one second cavity in communication with each of the first cavities, wherein the at least one second cavity has a cross-sectional area less than the cross-sectional area of the first cavity.

5. The method according to claim 4, wherein a depth of the first cavity and a depth of the at least one second cavity formed in communication with the first cavity equals the thickness of the barrier.

6. The method according to claim 4, wherein the first cavity and the at least one second cavity formed in communication with the first cavity are formed simultaneously.

* * * * *